US009662511B2

(12) United States Patent
Krechting (10) Patent No.: US 9,662,511 B2
(45) Date of Patent: May 30, 2017

(54) METHODS OF MAKING A MEDICAL APPLICATOR (71) Applicant: Nucletron Operations B.V., Veenendaal (NL)

(72) Inventor: Paulus Cornelis Hendrikus Maria Krechting, Veenedaal (NL)

(73) Assignee: Nucletron Operations B.V., Veenendaal (NL)

(*) Notice: Subject to any disclaimer, the term of this patent is extended or adjusted under 35 U.S.C. 154(b) by 160 days.

(21) Appl. No.: 14/437,305

(22) PCT Filed: Oct. 25, 2013

(86) PCT No.: PCT/IB2013/002634
§ 371 (c)(1),
(2) Date: Apr. 21, 2015

(87) PCT Pub. No.: WO2014/068398
PCT Pub. Date: May 8, 2014

(65) Prior Publication Data
US 2015/0265849 A1 Sep. 24, 2015

Related U.S. Application Data (60) Provisional application No. 61/722,573, filed on Nov. 5, 2012.

(51) Int. Cl.
*B29C 41/02* (2006.01)
*A61N 5/10* (2006.01)
(Continued)

(52) U.S. Cl.
CPC ............ *A61N 5/1016* (2013.01); *A61B 34/10* (2016.02); *B29C 33/3842* (2013.01);
(Continued)

(58) Field of Classification Search
CPC ............ B29C 33/3842; B29C 33/3857; B29C 33/3878; B29C 67/0051; B29C 67/0055; B29C 67/0059; B29C 67/0088
(Continued)

(56) References Cited

U.S. PATENT DOCUMENTS 7,571,728 B2   8/2009   Forman et al.
7,678,040 B2   3/2010   Francescatti et al.
(Continued)

OTHER PUBLICATIONS

Dong P. et al. "4Pi Radiation Therapy for Liver SBRT", International Journal of Radiation Oncology-Biology-Physics, S202:1092(2012).*
(Continued)

*Primary Examiner* — Leo B Tentoni
(74) *Attorney, Agent, or Firm* — Bookoff McAndrews, PLLC (57) ABSTRACT Embodiments of the disclosure are drawn to methods of forming an applicator body of an applicator for insertion into an anatomical cavity of a patient for delivering a treatment to the patient. In some instances, the method may include receiving a first three-dimensional image of the anatomical cavity, which was generated while the anatomical cavity contained an expandable container adjacent a tissue region of the patient, and while the expandable container was filled with fluid such that the container was expanded to substantially conform to the shape of at least a portion of the tissue region. The method also may include isolating, from the first three-dimensional image, a first sub-image corresponding to an image of the filled expanded container. The method further may include using the first sub-image as a design template for forming the applicator body for use with the patient.

20 Claims, 6 Drawing Sheets (51) Int. Cl.
    *B29C 33/38*     (2006.01)
    *B29C 67/00*     (2017.01)
    *B33Y 10/00*     (2015.01)
    *B33Y 80/00*     (2015.01)
    *B29L 31/00*     (2006.01)
    *A61B 34/10*     (2016.01)

(52) U.S. Cl.
    CPC ...... *B29C 33/3857* (2013.01); *B29C 33/3878* (2013.01); *B29C 67/0051* (2013.01); *B29C 67/0055* (2013.01); *B29C 67/0059* (2013.01); *B29C 67/0088* (2013.01); *A61B 2034/102* (2016.02); *A61N 2005/1018* (2013.01); *B29L 2031/7546* (2013.01); *B33Y 10/00* (2014.12); *B33Y 80/00* (2014.12); *F04C 2270/041* (2013.01)

(58) Field of Classification Search
    USPC ....... 264/113, 219, 220, 222, 225, 226, 227, 264/308, 313, 314, 401, 497; 700/118, 700/119, 120
    See application file for complete search history.

(56) References Cited

U.S. PATENT DOCUMENTS

| | | | |
|---|---|---|---|
| 7,688,938 B2 | 3/2010 | Paliwal et al. | |
| 7,726,318 B2 | 6/2010 | Francescatti et al. | |
| 7,727,137 B2 | 6/2010 | Francescatti et al. | |
| 7,744,521 B2 | 6/2010 | Francescatti et al. | |
| 7,783,006 B2 | 8/2010 | Stewart et al. | |
| 7,815,561 B2 | 10/2010 | Forman et al. | |
| 7,885,382 B2 | 2/2011 | Stewart et al. | |
| 7,914,434 B2 | 3/2011 | Francescatti et al. | |
| 2003/0006534 A1* | 1/2003 | Taboas | B29C 33/3842 264/401 |
| 2007/0276501 A1* | 11/2007 | Betz | A61F 2/30942 264/222 X |
| 2008/0300445 A1 | 12/2008 | Francescatti et al. | |
| 2010/0204534 A1* | 8/2010 | Damarati | A61M 25/0029 600/3 |

OTHER PUBLICATIONS

Dong, P et al., "4π Noncoplanar Stereotactic Body Radiation Therapy for Centrally Located or Larger Lung Tumors," *International Journal of Radiation Oncology-Biology-Physics*, vol. 86, No. 3, pp. 407-413, 2013, www.redjournal.org, © Elsevier Inc.

Thomas, M. A. et al., "Multidimensional MR Spectroscopic Imaging of Prostate Cancer In Vivo," *NMR in Biomedicine*, 2014, 27:53-66, Copyright © 2013 John Wiley & Sons, Ltd., www.wileyonlinelibrary.com.

"Novel Method for the Rapid Fabrication of Brachytherapy Applicators," *UCLA Technologies Available for Licensing*, http:/www.oip.ucla.edu, Copyright © 2012 The Regents of the University of California, 1 page.

\* cited by examiner

METHODS OF MAKING A MEDICAL APPLICATOR

CROSS-REFERENCE TO RELATED APPLICATIONS

This patent application is a U.S. national stage of International Patent Application No. PCT/IB2013/002634, filed Oct. 25, 2013, which claims the benefit of priority to U.S. Provisional Application No. 61/722,573, filed Nov. 5, 2012, both of which are incorporated herein by reference in their entireties.

FIELD OF THE INVENTION

Embodiments of the present disclosure relate to applicators, and more particularly, to brachytherapy applicators for positioning one or more catheters or needles at a predetermined area of tissue.

BACKGROUND OF THE INVENTION

Brachytherapy is a method of treating cancer by placing radioactive sources either into or next to an area of tissue requiring treatment. Delivering radiation directly to the target treatment area may allow a clinician to administer higher doses of radiation while decreasing the impact on surrounding, healthy tissue.

During treatment, a brachytherapy applicator may be positioned adjacent the target treatment area. The applicator may be used to align catheters and/or needles with the treatment area and position them for the delivery of radioactive sources to the target tissue. Catheters incorporated in the applicator may be connected to a source of treatment, for example, an afterloader, and forms of treatment, such as radioactive sources, may be delivered from the source, through the catheters or needles, and to the treatment area.

To increase the effectiveness of brachytherapy, clinicians may aim to administer an optimal dosage of radioactive sources to the target tissue. Movement or misalignment of the applicator may affect the amount of radiation delivered to the target tissue. Misalignment could cause delivery of treatment to the wrong area or dissipation of treatment before contacting the target area. If the applicator does not fit the contours of the patient's anatomy, the applicator may be more likely to shift. Even if it stays in place, the applicator may not be able to contact optimal portions of the target tissue. While applicators may be available in different sizes, variations in patient anatomy, tumor location, tumor growth, and disease state may hinder the ability of even an appropriately sized applicator from delivering an optimal dosage of treatment. Further, a limited selection of applicator types and configurations may confine the number treatment regimens available to a clinician. Thus, there exists a need for an easy-to-form applicator capable of conforming to the unique size, shape, and dosage requirements of each individual patient to optimize catheter positioning, and thus treatment delivery, for optimizing patient treatment plans.

SUMMARY OF THE INVENTION

Embodiments of the present disclosure are directed to a method of forming a medical applicator.

In accordance with one embodiment, a method of forming an applicator for insertion into an anatomical cavity of a patient for delivering a treatment to the patient may include receiving a three-dimensional image of the anatomical cavity. The three-dimensional image may be generated while the anatomical cavity contains an expandable container adjacent a tissue region of the patient, wherein the container, when contained in the anatomical cavity, is expanded to substantially conform to the shape of at least a portion of the tissue region forming at least a portion of the anatomical cavity. The method may further include isolating, from the three-dimensional image, a first sub-image corresponding to an image of the filled expanded container and using the sub-image as a design template for forming the applicator for use with the patient.

Various embodiments of the disclosure may include one or more aspects: the method may further comprise sending the sub-image to a three-dimensional printer to form the applicator and forming the applicator with the three-dimensional printer, using the sub-image as the template for the three-dimensional printer; the method may further include operating a magnetic resonance imaging device to obtain the three-dimensional image; the anatomical cavity may be a vaginal cavity; the applicator may be configured to deliver a dose of treatment to the tissue region; the applicator may be a brachytherapy applicator and the treatment may be radiation; the fluid may be saline; the method may further include obtaining a second image of the expanded container using the second image and the first image as a design template to form the applicator; the container may be expanded to a first pressure when the first image is taken, and the container may be expanded to a second pressure different from the first pressure when the second image is taken; using the sub-image as a template for forming the applicator may further include processing data from the sub-image to determine the location of at least one feature of the applicator that is used for delivery of treatment to the patient; the at least one feature may include a channel for delivering the treatment via the applicator to the patient; the channel may be configured to guide at least one of a catheter and a needle to a portion of the region of tissue in the anatomical cavity; the at least one feature may include an opening in the applicator that is configured to deliver the treatment; the processing may include the use of at least one algorithm for determining the location of the at least one feature of the applicator; the at least one feature may be formed by the three-dimensional printer when forming the applicator; the at least one feature may be formed after the three-dimensional printer has formed the applicator; and the method may further include inserting at least one of the catheter and the needle in at least one channel after the applicator is formed.

In one embodiment of the present disclosure, a method of forming an applicator to be used for providing radiation treatment to a patient may include placing an expandable container into a body cavity of a patient. The method may further include filling the expandable container with fluid such that the container expands to fill the body cavity, and an external surface of the container substantially conforms to the shape of the body cavity. A first image may be obtained of the expanded container placed in the patient, and the shape of the expanded container in the first image may be used to determine the shape of the body cavity. The method may also include configuring the overall shape of the applicator based on the determined shape of the body cavity.

Various embodiments of the disclosure may include one or more aspects: the method may further include determining the location of at least one treatment channel in the applicator for delivering the radiation treatment to the patient, wherein the location of the treatment channel is determined based on the determined shape of the body cavity and based on a determined location in the first image of an anatomical portion of the patient requiring treatment; and the method may also include determining the number of treatment channels to be included in the applicator based on the determined shape of the anatomical cavity from the first image.

Additional objects and advantages of the embodiments will be set forth in part in the description that follows, and in part will be obvious from the description, or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention, and together with the description, serve to explain the principles of the invention.

DETAILED DESCRIPTION

Reference will now be made in detail to the exemplary embodiments of the present disclosure described below and illustrated in the accompanying drawings. Wherever possible, the same reference numbers will be used throughout the drawings to refer to same or like parts. For purposes of this disclosure, "proximal" refers to an end closer to the clinician during use, and "distal" refers to an end further from the clinician during use.

While the present disclosure is described herein with reference to illustrative embodiments for particular applications, such as brachytherapy applicators for gynecological use, it should be understood that the embodiments described herein are not limited thereto. Those having ordinary skill in the art and access to the teachings provided herein will recognize additional modifications, applications, embodiments, and substitution of equivalents that all fall within the scope of the invention. For example, the principles described herein may be used with any suitable applicator (e.g., for use with injection needles, catheters, or biopsy needles) for any suitable treatment or diagnostic purpose (e.g., brachytherapy, biopsies, or drug delivery) and for any suitable part of the human anatomy (e.g., internal body cavities or superficial regions). Accordingly, the invention is not to be considered as limited by the foregoing or following descriptions.

Other features and advantages and potential uses of the present disclosure will become apparent to someone skilled in the art from the following description of the disclosure, which refers to the accompanying drawings.

Figure 1A:
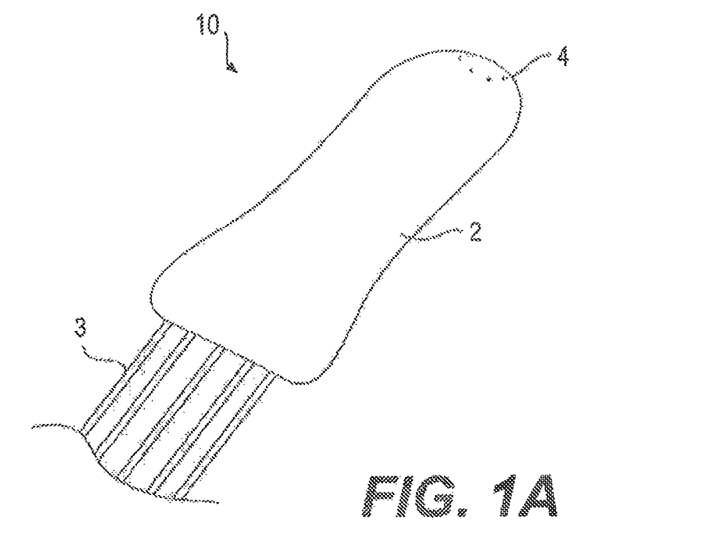
FIG. 1A illustrates an exemplary applicator, according to an embodiment of the present disclosure.

FIG. 1A illustrates an exemplary brachytherapy applicator 10. Applicator 10 may include an applicator body 2 through which one or more catheters 3 may extend. Applicator body 2 may be hollow or may be substantially solid and may include a number of channels for catheters 3 to pass through. If hollow, applicator body 2 may have a closed, distal end as well as an open, proximal end through which catheters 3 extend, or applicator body 2 may have two open ends. Applicator body 2 may be sized and shaped to fit into a body cavity (e.g., to contact tissue in a vaginal or anal cavity), or applicator body 2 may be configured for contacting a superficial surface of the body (e.g., a patient's chest or abdomen). For example, in some embodiments, applicator body 2 may be generally cylindrical, and in some embodiments, applicator body 2 may be irregularly shaped.

Applicator body 2 may be rigid or deformable, or may have both rigid and deformable regions. In some embodiments, inclusion of deformable regions may increase patient comfort or increase contact with the surrounding tissue. Applicator body 2 may be formed of any suitable material, including, e.g., glass, plastic (with or without fillers, e.g., liquid silicone rubber, polyetheretherketone, polyphenylsulfone, polycarbonate, and/or polyoxymethylene), ceramic, metal (e.g., stainless steel, titanium, nitinol, tungsten) or metal alloys, composite fibers, or any suitable combination of materials. In some embodiments, applicator body 2 may be formed of a material capable of being detected by an imaging system or decreasing distortion when viewed by an imaging system, such as an MRI or CT image. In some embodiments, applicator 20 may include positioning sensors or image tracking devices to check correct placement, or an MRI or other suitable imaging means may be used to check placement.

In some embodiments, applicator 10 may be formed of more than one type of material, for example, both rigid and deformable materials. Different materials may be layered or may form different regions of applicator body 2. Applicator 10 may also include materials suitable for shielding. In embodiments in which applicator 10 is configured to deliver radioactive substances, applicator 10 may include one or more portions of applicator body 2 formed of a suitable shielding material to reduce radiation exposure of healthy tissue or organs. For example, titanium or tungsten, or alloys thereof, may form portions of applicator body 2 to improve shielding. In other embodiments, applicator 10 may be formed of one material.

Additionally, applicator 10 may include any suitable coating, or any suitable combination of coatings. For example, applicator body 2 may include a lubricious coating to aid insertion into a patient. In some embodiments, applicator body 2 may include a drug eluting, anticoagulant, antiseptic, or anesthetic coating, for example. In some embodiments, applicator body 2 may include a coating capable of being imaged via a camera or imaging system. This may allow a clinician to view the position of applicator 10 within the patient once inserted. In some embodiments, applicator body 10 may be formed of a material capable of being imaged or may include embedded markers for imaging-assisted insertion or placement.

Catheters 3 may extend through an open end of applicator 10 and along an inner portion of applicator body 2. A proximal end of catheters 3 (not shown) may connect to a treatment dispenser, such as an afterloader for dispensing radioactive materials into catheters 3. The afterloader may dispense a form of treatment, e.g., radiation, through catheters 3 and into applicator 10. A distal end of catheters 3 may connect to openings 4 in applicator body 2. Treatment materials may flow through catheters 3 in applicator 10 and out of openings 4 to a region external to applicator 10. Applicator body 2 may be configured to align catheters 3 so as to position the distal ends of catheters 3 adjacent a treatment tissue site. The radiation may exit applicator body 2 and catheters 3 through openings 4 to administer a dose of treatment at the target tissue location.

Catheters 3 may be formed of any suitable material, for example, metal or plastic, or a combination thereof, and may be rigid or flexible, or may have rigid and flexible portions. Catheters 3 may have any suitable cross-sectional shape and size. For example, catheters 3 may have a circular, rectangular, or oval cross-sectional shape, and may vary in size (e.g., length or width) depending on the desired pressure, amount, and/or rate of dosage to be delivered to a treatment site. Further, applicator 10 may include different types of catheters. While the exemplary embodiment of FIG. 1A depicts five catheters 3, applicator 10 may include any suitable number of catheters 3, for example, a single catheter or eight catheters. The number of catheters 3 may be determined based on the target location, target area size, or disease state, for example. Further, catheters 3 may be removably attached to applicator body 2, or may be permanently attached to applicator body 2. For example, if catheters 3 are removable, applicator 10 may be reconfigured to include only the number of catheters necessary for a given patient at a given time.

If applicator body 2 is hollow, openings 4 may extend from an inner surface of applicator body 2 to an outer surface of applicator body 2. If applicator body 2 is substantially solid, openings 4 may be an extension of channels inside of applicator body 2, through which catheters 3 may extend. Openings 4 may be of any suitable size or cross-sectional shape, as described above in reference to catheters 3. Openings 4 may be configured to receive a portion of catheters 3. In some embodiments, openings 4 may have a substantially similar size or similar cross-sectional shape as the catheters they receive, and in some embodiments, openings 4 may have a different size or shape. For example, connector elements may connect catheters 3 to openings 4, allowing for differences in shape or size. In some embodiments, there may be a one-to-one ratio of catheters 3 to openings 4, while in other embodiments, there may be more or less catheters 3 than openings 4.

Figure 1B:
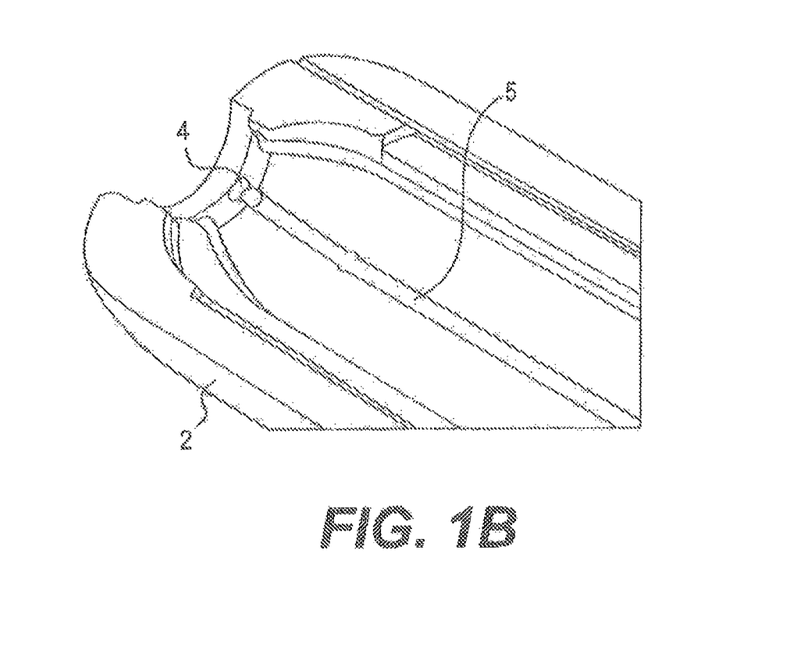
FIG. 1B illustrates an exploded, cross-sectional view of a distal region of the applicator of FIG. 1A, according to an embodiment of the present disclosure.

As shown in FIG. 1B, an interior region of applicator body 2 may include a number of channels 5. Channels 5 may include grooves or inlets within applicator body 2. Channels 5 may be configured to receive one or more catheters 3. A channel 5 may substantially surround a circumference of catheter 3, or a channel 5 may be configured to surround a portion of the circumference of a catheter 3, or a combination thereof. Channels 5 may extend a portion of the length of applicator body 2. In some embodiments, channels 5 may extend from a proximal end of applicator body 2 to openings 4 located in a more distal region of applicator body 2. In some embodiments, channels 5 may extend through only a portion of applicator body 2. Channels 5 may extend substantially longitudinally or substantially horizontally along applicator body 2, or may form patterns or irregular paths along applicator body 2. Channels 5 may be positioned to align catheters 3 so as to optimize positioning of catheters 3, for example, placement and angle, for the delivery of treatment to a target area of tissue.

In some embodiments, one or more channels 5 may be configured to receive one or more visualization devices. For example, a fiberscope or suitable visualization device may be included in a channel 5 to provide visual guidance during insertion or removal of applicator 10, or to provide visual confirmation of treatment delivery or for visualization of the targeted tissue, for example. A visualization device may be removably or permanently housed in channel 5. In one embodiment, a channel 5 may be included to guide a fiberscope to an opening in or towards the uterus.

Applicator body 2 may include any suitable number of channels 5. There may be a direct one-to-one correlation between the number of catheters 3 in applicator 10 and the number of channels in applicator body 2. In other embodiments, some catheters 3 may not be confined to a channel, and there may be more catheters 3 than channels 5. In still other embodiments, applicator body 2 may have more channels than catheters, for example, to allow a clinician to switch catheters 3 into and out of different channels.

Channels 5 may have any suitable shape or size for receiving catheters 3. The size and shape of channels 5 may substantially correspond to that of catheters 3, or may be different. Channels 5 may be curved or straight, or may include both curved and straight portions. Catheters 3 may be permanently coupled to channels 5, or may be removable from channels 5. Catheters 3 may be maintained in channels 5 by any suitable means, for example, via a snap-fit, twist-fit, friction-fit, adhesives, glue, or fusing the catheters to the channels 5.

Figure 2:
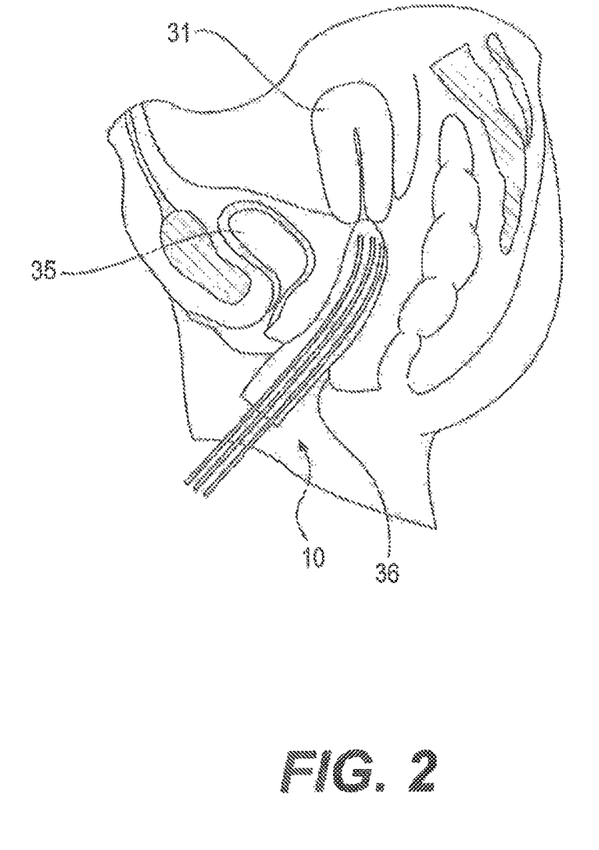
FIG. 2 illustrates a cross-sectional view of an exemplary applicator inserted into the body of a patient, according to an embodiment of the present disclosure.

FIG. 2 shows applicator 10 inserted into vaginal cavity 36 of a patient. In this exemplary gynecological embodiment, applicator 10 may be inserted so as to contact a cervical portion of uterus 31. When applicator 10 is positioned within cavity 36, catheters 3 may align with a target portion of tissue, e.g., abnormal tissue, so as to deliver a dosage of treatment directly to the target tissue. To promote proper dosage delivery, catheters and openings 4 may directly contact the target area at an optimum angle and location to administer the dosage to the correct tissue region. As discussed above, misalignment of applicator 10 with the target treatment area may reduce the dosage amount delivered to the area, reducing the efficacy of treatment. Misalignment may also increase exposure of healthy tissue, including, e.g., organs such as bladder 35 and/or uterus 31, to the treatment dose, causing unnecessary side effects or injury to other, healthy regions. The anatomy, target size and location, and disease state, e.g., may vary between patients, so using a standard applicator for every patient may not allow for optimized dosing even when correctly aligned. Further, when a standard applicator does not match the contours of a patient's anatomy, gaps may allow the applicator to shift or may position the catheters further from the target tissue than may be desirable. To compensate, clinicians may use packing or other means to stabilize a standard applicator 10, which may increase procedure time, decrease patient comfort, and decrease the accuracy of dosage delivery.

To increase treatment efficacy, applicator 10 may be customized, by using methodologies consistent with the present disclosure, to correspond to the unique anatomy of an individual patient. Forming applicator 10 to mirror the contours of a patient's body cavity may promote proper alignment. Further, the placement of an applicator and delivery of treatment may be tailored to the specific needs of the individual patient. This may expand the number of treatment plan options available to a clinician. For example, the fit of applicator 10, or the number, location, angle, shape, size, and type of catheters 3, and dosages can all be mixed and matched to create a customized treatment regime using custom applicator 10.

Figure 3:
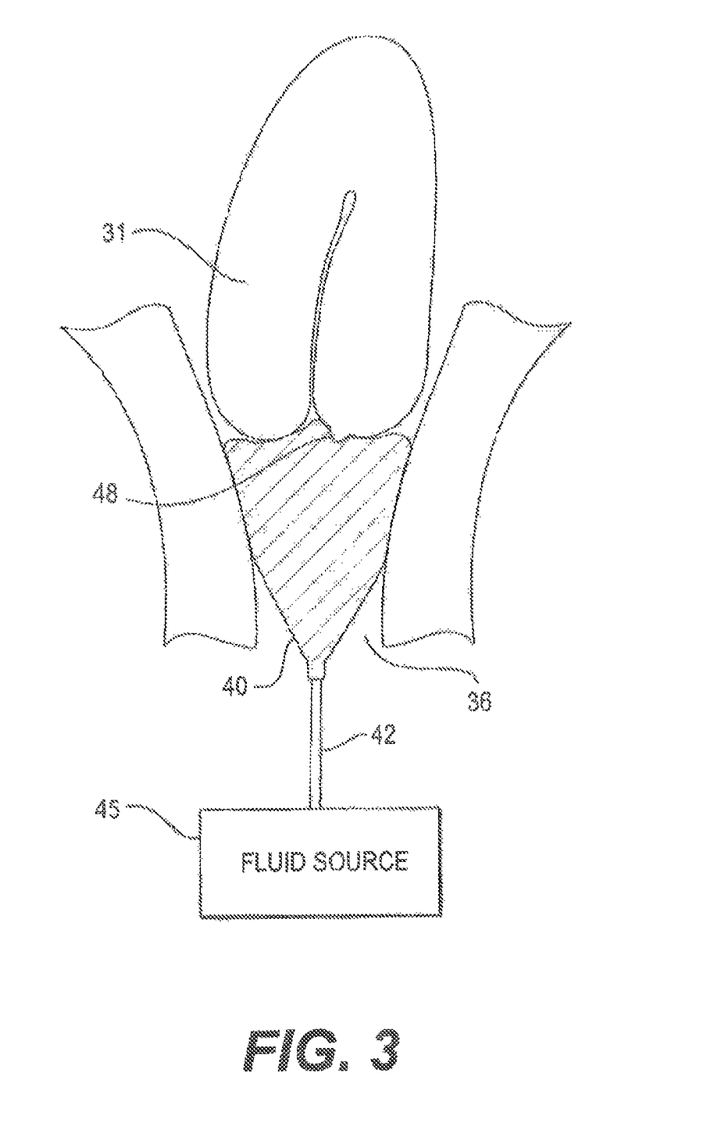
FIG. 3 illustrates an exemplary step in the method of forming a custom applicator, according to an embodiment of the present disclosure.
Figure 4:
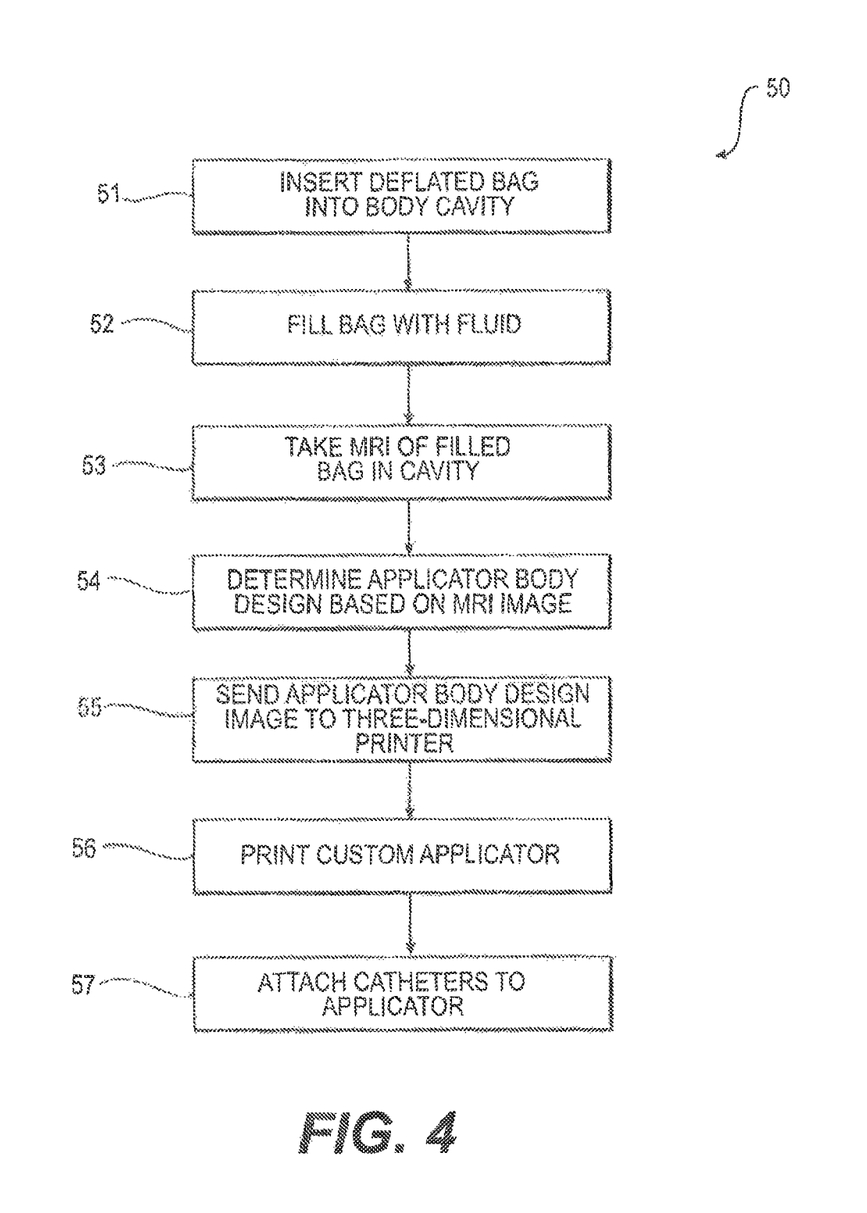
FIG. 4 illustrates a flow chart depicting an exemplary method of forming a custom applicator, according to an embodiment of the present disclosure.

To generate a custom applicator according to the present disclosure, a clinician may map the anatomy of a patient and create a template reflecting the contours of the patient. FIG. 4 generally illustrates a flow chart depicting an exemplary custom-applicator production process 50. In one embodiment, to generate a template of an internal cavity, a clinician may insert a flexible, expandable container, such as a balloon or bag, into the cavity of interest. As depicted in FIG. 3, bag 40 may be inserted into vaginal cavity 36. Bag 40 may be operably connected to a fluid source 45, either directly, or via a delivery device 42. Delivery device 42 may be flexible or rigid, for example, a flexible or rigid tube, such as a catheter, a needle, a tube, a hose, or any suitable device. In some embodiments, bag 40, fluid deliver device 42, or fluid source 45 may include one or more sensors, for example, a position sensor or pressure gauge. Once bag 40 is in position (step 51 of FIG. 4), fluid, such as gas or liquid, may be transferred into bag 40, causing bag 40 to expand (step 52). In some embodiments, fluid source 45 may deliver water, saline, or air, for example, into bag 40. Bag 40 may be filled with fluid until a predetermined pressure has been reached, as described further below.

As bag 40 expands, the outer surface of the bag may press up against adjacent tissue. In this manner, bag 40 may conform to the shape of the cavity as bag 40 fills with fluid. For example, in FIG. 3, bag 40 has expanded to conform against the walls of vaginal cavity 36 and a portion of uterus 31. Accordingly, the shape of bag 40 may substantially mimic the anatomy of vaginal cavity 36. As depicted in FIG. 3, uterus 31 or a cervical region may include an abnormality 48. Abnormality 48 may be an area of tissue targeted for treatment, for example, a tumor or cist. As discussed herein, by expanding bag 40, the surface of bag 40 may reflect the size, shape, and orientation of abnormality 48 and the surrounding tissue of vaginal cavity 36.

Once bag 40 has been expanded to contact the walls of vaginal cavity 36, the vaginal cavity may be mapped and a template of the cavity may be generated. In some embodiments, bag 40 may include a position sensor or imaging marker to allow a clinician to determine whether bag 40 is fully inserted or is contacting the proper regions before creating a template of vaginal cavity 36 for the creation of applicator 10.

A clinician may then use an imaging system, such as a CT image, ultrasound image, PET image, X-ray image, fluorescence image, or MRI to detect the contours of bag 40. In some embodiments, bag 40 may be formed of a material capable of being detected by a type of imaging system. For example, bag 40 may be formed of a material capable of fluorescing, such that an imaging device can detect the location and/or boundaries of the bag. In the exemplary embodiment of FIG. 4, an MRI is conducted to detect the borders of expanded bag 40 (step 53) to determine the size and shape of vaginal cavity 36. The image may also be used to detect the location of surrounding tissue and organs. The image may be used as a mold for creating a custom-fit applicator that may correspond to the specific patient's anatomy. Using filled bag 40 when conducting the imaging step may also increase the resolution of the image and allow a clinician to more accurately determine the patient anatomy and the size, shape, and location of abnormality 48.

In some embodiments, steps 51 through 53 may be repeated to gain additional information for forming applicator 10, or to double-check the accuracy of the first assessment. For example, a clinician may fill bag 40 with fluid until a certain, predetermined pressure within bag 40 is achieved. An MRI may be taken at this first fill pressure. A clinician may then increase or decrease the fill level, and thus the pressure, inside bag 40 and take a second MRI at the second, different pressure. This process may be repeated any suitable number of times and at any suitable number of pressure levels of the fluid in bag 40. This information may assist a clinician in creating an applicator template corresponding to the anatomy of a patient. For example, the position of bag 40 at different pressure levels may indicate the deformability or rigidity of different regions of anatomy in vaginal cavity 36. Repeating steps 51-53 may also give a clinician a more accurate depiction of the projected location of abnormality 48 in relation to applicator 10. In some embodiments, the position of bag 40 at different pressures may be merged or averaged to determine a suitable shape and size of applicator 10. Using the one or more MRI images, a clinician may be able to determine the appropriate size and shape of applicator 10 suitable for that specific patient.

A clinician may next analyze the three-dimensional image of bag 40 (step 54), assessing, e.g., the size, location, and relative anatomy of abnormality 48 and vaginal cavity 36 to determine the appropriate applicator body design, such as the optimal placement and number of catheters 3 to include in applicator 10. By visualizing the topography of vaginal cavity 36 and abnormality 48, a clinician may be able to more accurately guide catheters 3 for the delivery of treatment. The clinician may vary, e.g., the angle, size (width and length), and arrangement of catheters 3 in applicator body 2 to promote the optimal dosage delivery to the target region. Based on the location, angle, size, and disease state of abnormality 48, a clinician may adjust the dosage amount or treatment type to deliver to different areas. In some embodiments, the clinician may view the image to determine the optimal distribution of catheters 3. In some embodiments, a clinician may assess the relative positioning of organs or other anatomical structures to determine the desired location or angle of shielding portions in applicator body 2 so as to decrease exposure of these structures to treatments, such as radiation. Using this information, a clinician may be able to create and tailor an applicator body design and treatment plan customized to the individual patient.

In some embodiments, the clinician may use techniques known in the art to identify or determine a desired catheter distribution and a dosage treatment plan to be implemented by the applicator 10. For example, a preliminary catheter distribution and dosage treatment plan may be determined based on a clinician's analysis of the patient. A processor (not shown) may then be used to analyze and calculate the optimal catheter and dose distribution within the applicator 10. In one embodiment, an MRI machine may be physically or wirelessly coupled to a processor, for analyzing and/or storing the three-dimensional image. When determining the placement of catheters 3 in applicator body 2, either the clinician or the processor may also determine the location and orientation of channels 5 and openings 14 to be included in applicator 10 in order to achieve the desired arrangement of catheters 3. For instance, the processor may modify the three-dimensional image information to include the structural and positional information associated with the catheters 3, including channels 5 and openings 14, in applicator 10. As described below, the modified three-dimensional image information can then be output to a three-dimensional printer for fabrication of applicator 10.

Further, depending on the size, location, and disease state, a clinician or processor may determine the number of catheters 3 that may be included in applicator 10 and the dosage size that each catheter 3 should be configured to deliver. In some embodiments, a processor may decide that each catheter should deliver the same dosage amount. In some embodiments, a processor may decide that different catheters should deliver different dosage amounts. The delivery of treatment to different areas of the patient's anatomy may be customized, including, e.g., customization of the amount, pressure, rate, or type of treatment delivered by each catheter. In some embodiments, catheters 3 may be loaded separately from a treatment source, allowing for customization of each catheter 3 to the variations in anatomy for a given patient. In one embodiment, a processor may be used to analyze the three-dimensional image to generate a corresponding three-dimensional map of an applicator design, including the placement of channels 5 and openings 14. In one embodiment, a processor may determine the coordinates of various anatomical structures, e.g., a tumor, and calculate corresponding coordinates for the placement of channels 5 in applicator 10, creating a three-dimensional data file reflecting the design of a customized applicator body 2.

Increasing the ability to place and fit applicator 10 may improve the clinician's knowledge of and thus control over dose delivery and treatment planning. This may thus allow a clinician to customize the positioning, type, and size of different catheters in applicator 10. Applicator 10 may then be formed so as to accommodate the unique arrangements and configurations, ranging from simple to complex. In this way, custom applicator 10 may expand the number of treatment options available to a clinician.

Once the data for the desired placement, number, and size of catheters 3 and the corresponding arrangement of channels 5 is determined, a three-dimensional data file of the applicator body design may be sent to a three-dimensional printer (step 55) to form applicator body 2. The three-dimensional printer may be on location, or may be remote from the patient and clinician. For example, the image data may be sent to a manufacturer for three-dimensional printing. The three-dimensional printer may use the data to generate, or 'print,' a three-dimensional applicator body 2 that replicates the contours of the patient's unique anatomy (step 56), so that applicator 10 may align with the anatomy of the patient when inserted. This alignment may maximize contact between applicator 10 and vaginal cavity 36 of the patient. The precision of a three-dimensional printer may allow for greater accuracy, and thus improved fit, when forming applicator body 2.

The three-dimensional printer may also be configured to form channels 5 in applicator body 2 during the printing process. The three-dimensional printing technology may allow for precise recreation of the anatomy and precise placement of channels 5 and openings 4 within applicator body 2. Using a three-dimensional printer may allow a clinician to include any suitable arrangement of channels 5, including complicated patterns with varying angles or channel depths, to increase the accuracy with which catheters are directed to the target treatment area. Complex shapes and configurations of applicator body 2 and channels 5 can be achieved through the use of three-dimensional printing, which may allow a manufacturer to more quickly, affordably, and efficiently produce a large number of different customized applicators. In other embodiments, a three-dimensional printer may form applicator body 2 without channels 5 or without openings 4. In such an embodiment, channels 5 and openings 4 may be formed after printing, with, for example, a tool such as a drill or a laser.

Once applicator body 2 and channels 5 are formed, a manufacturer or a clinician may insert catheters 3 into channels 5 (step 57). In some embodiments, a three-dimensional printer may produce separate sections of applicator body 2 to allow easier placement of catheters 3, which may then be assembled once catheters 3 are in place. In one embodiment, the three-dimensional printer may produce two halves of applicator body 2. A manufacturer or clinician may place catheters 3 in their respective channels 5 and then attach the two halves, for example, with mechanical attachments or adhesives, or by heat fusing the sections together. In other embodiments, applicator body 2 may be monolithically formed. Applicator 10 may then be sterilized, packaged (if printed remotely), and prepared for use.

As discussed above, catheters 3 may be permanently or removably placed in channels 5 using any suitable fixation mechanism. In some embodiments, catheters 3 may be permanently fixed within channels 5. For example, applicator 10 may be a disposable, or single-use, applicator, and catheters 3 may be disposed of with applicator body 2. In one embodiment, catheters 3 may be removable and applicator 10 may be a reusable applicator. For example, catheters 3 may be removed and disposed of between uses, then replaced with new catheters 3. In other embodiments, catheters 3 may be removed and sterilized between uses, then reinserted into applicator 10. In other embodiments, applicator may be reusable, and catheters 3 may remain within channels 5 during sterilization.

A patient may undergo brachytherapy treatment once during a treatment regimen or may attend multiple treatment sessions to administer radiation to a target tissue site. If applicator 10 is a single-use applicator, then a new applicator 10 may be generated for each treatment session. The same template may be used each time to generate a new applicator, or multiple applicators may be generated during the initial measurement process and then used over the course of the different sessions. In some embodiments, the measuring process may be repeated before different treatment sessions to create an optimized applicator customized for that particular patient at that particular treatment stage, for example, to adjust for changes in tumor size or location or patient anatomy at the time of the session. Disposable, built-to-order applicators may eliminate the need to carry inventory and the need to maintain costly sterilization equipment. If applicator 10 is reusable, then applicator 10 or portions of applicator 10 may be sterilized after each session and reused when that patient returns.

In some embodiments, applicator 10 may be assigned a unique identifier to identify the applicator as belonging to a particular patient. For example, an identifier may allow a manufacturer or a clinician to determine which applicator 10 a patient was customized for. The identifier may include a marking or unique code, e.g., a barcode, or alphanumeric code, included on applicator 10. In some embodiments, the identifier may be a radio-frequency identification (RFID) tag included in applicator 10. The RFID may be embedded in applicator body 2, or may be included on or in applicator 10. In a reusable applicator, the identifier may allow a clinician to keep track of and use the correct custom applicator 10 for the correct corresponding patient. In a disposable or a reusable embodiment, the identifier may allow a manufacturer or clinician to provide an easy means of tracking and determining which patient an applicator 10 was customized for.

Figure 5A:
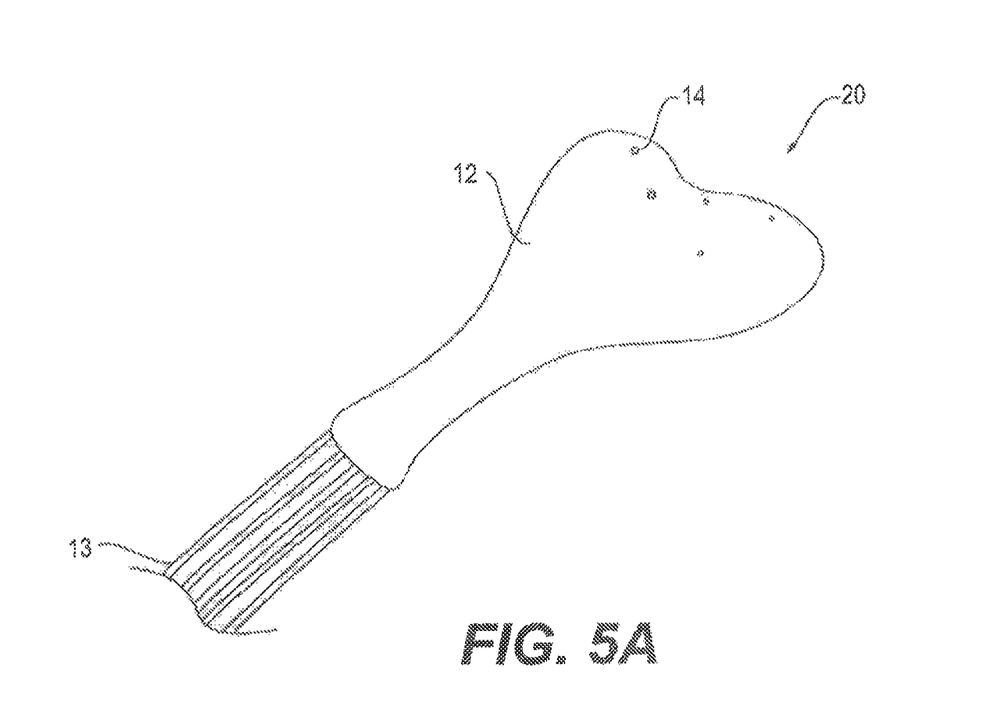
FIG. 5A illustrates an exemplary applicator, according to an embodiment of the present disclosure.
Figure 5B:
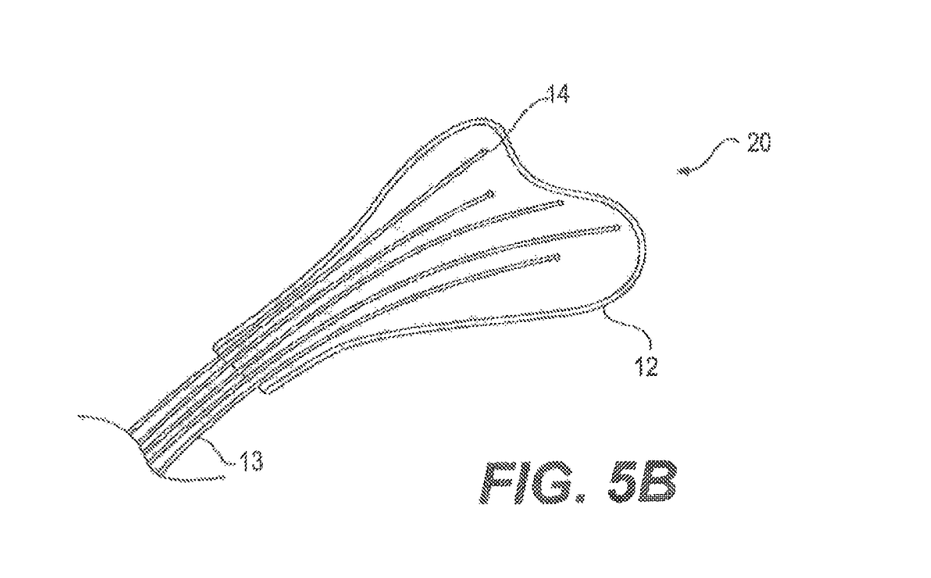
FIG. 5B illustrates an exemplary cross-section of the applicator of FIG. 5A, according to an embodiment of the present disclosure.

FIGS. 5A and 5B depict inner and outer portions of an exemplary custom applicator 20. Applicator body 12 may be sized and shaped according to process 50 (FIG. 4) so as to reflect the contours of a patient's anatomy. Applicator 20 may include any suitable number of catheters 3 in a suitable configuration for that particular patient. Customizing the fit of applicator 20 within vaginal cavity 36 may allow for more consistent and more precise placement of applicator 20. This may make it possible for a clinician to use more complex arrangements of catheters 3, because the clinician can tailor the arrangement to the patient and may be able to better predict and control the placement and delivery of treatment, for example, radiation. Because the shape of custom applicator 20 may conform to the shape of the patient, placement may be simplified because applicator 20 may only 'fit' one way when inserted into a patient. This can reduce misalignment errors and decrease procedure time, because placement may not need to be checked via other imaging techniques.

Improved fit may also decrease the likelihood that applicator 20 may shift due to movement either by the clinician or by the patient. For example, a patient may be able to move without applicator 20 shifting.

Improved fit may further allow clinicians to form applicators having different surfaces, for example, by incorporating a textured surface to hold applicator 20 in place. In some embodiments, applicator 20 may include openings or perforations configured to allow bodily fluids, e.g., vaginal mucosa, to seep into the device, decreasing the risk of displacement. Some embodiments may include projections configured to contact specific regions, for example, to provide a close fit with the tissue in some places while creating gaps or passages between the tissue and applicator 20 in other places.

For example, applicator 20 may be shaped so as to create a space between applicator 20 and an area of tissue. A treatment dose, local anesthetic, or imaging agent, e.g., may be released from an opening 14 located within the gap-forming portion of applicator 20. This may allow applicator 20 to maintain a pool of fluid or solid materials adjacent a region of tissue while applicator 20 is inserted into a patient. In some embodiments, an anesthetic may be pooled, and once the tissue is numbed, a needle 17 (shown in FIG. 5C and discussed further below) may be extended through opening 14 and into the numbed tissue. In another embodiment, an imaging agent may be pooled, allowing a clinician to check the position or fit of applicator 20, for example, migration of the imaging agent from the pool may indicate misalignment or an improper fit or applicator 20 with the patient. In still other embodiments, applicator 20 may include ridges or grooves on an exterior surface to form passages between the tissue and applicator 20. Such passages may allow for circulation of fluids, for example antiseptics or bodily fluids, around the applicator, or for the flow of treatment to predetermined areas. In some embodiments, a catheter 3 included in applicator 20 may be configured to deliver a source of non-treatment fluid, such as antiseptics, for circulation around applicator 20.

In some embodiments, a customized fit may allow a clinician to form an applicator having one or more insertion projections extending from an outer surface of applicator body 12. The customized shape of applicator 20 may make it easier for a clinician to align projection portions of applicator 20 with the corresponding areas of target tissue when compared to a standard, uniform, off-the-shelf applicator. For example, in the embodiment depicted in FIG. 5C, applicator 20 may include one or more needles 17. Needles 17 may include any suitable type of needle or projection, for example, an injection needle, a biopsy needle, or intravenous catheter, or combination thereof. Needles 17 may be fluidly coupled to catheters 13 and may project from openings 14 in applicator body 12. Needles 17 may project through openings 14 during insertion of applicator 20, or needles 17 may be configured to exit openings 14 and protrude once applicator 20 is in place. Needles 17 may have any suitable tip for contacting or penetrating tissue. In some embodiments, needles 17 may have a sharp tip to enable easy penetration of the tissue or a round tip for increased patient safety during treatment. In some embodiments, needles 17 may not be hollow. For example, needles 17 may not be used for delivery of treatment and may be used to anchor applicator 20 during dosage delivery. In such an embodiment, there may be fewer needles 17 than there are openings 14 or catheters 13. Any suitable number of needles 17 or projections may be used.

Figure 5C:
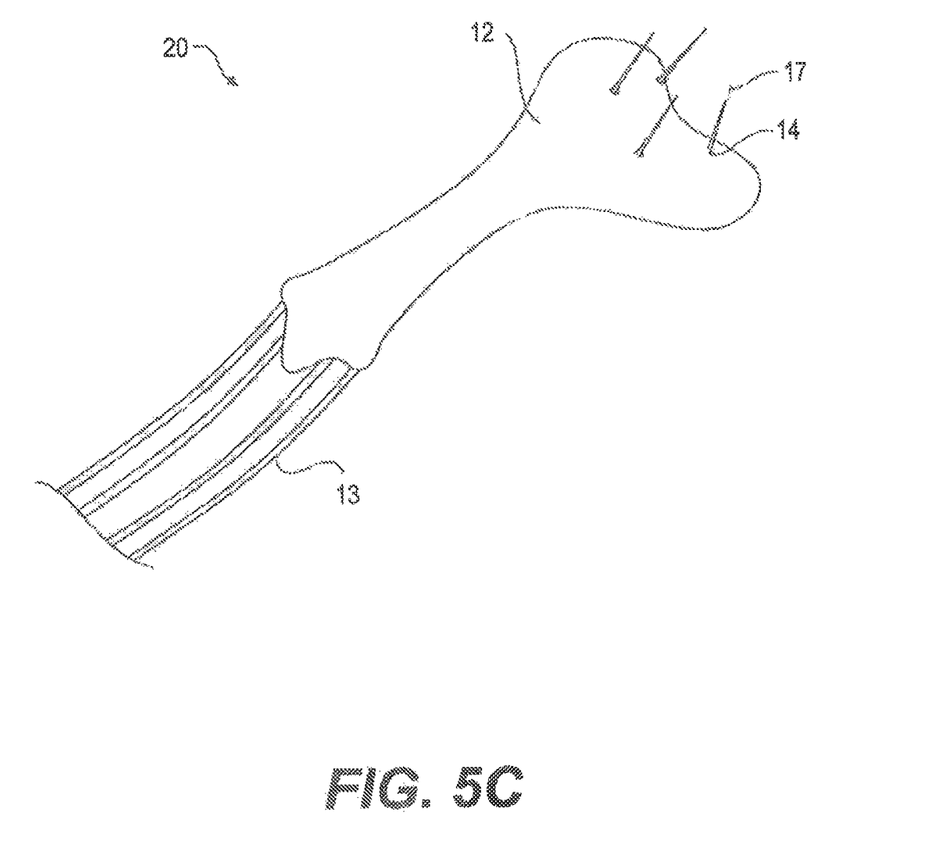
FIG. 5C illustrates an exemplary applicator, according to an embodiment of the present disclosure.

Needles 17 may be hollow and may be configured to contact or penetrate a portion of tissue, e.g., the target tissue to be treated, to allow more precise delivery of treatment to a target area. For example, applicator 20 may be inserted into a patient such that needles 17 penetrate a diseased target portion of tissue, such as a cancerous growth, e.g., a tumor. Radiation sources may be delivered from an afterloader, through catheters 13, through needles 17, and into an interior region of the tumor. This may allow a clinician to deliver a dose of radiation from within the tumor, reducing the exposure of healthy tissue to radiation and allowing for a more precise and potentially higher dose of radiation to the target treatment area.

In some embodiments, needles 17 may permanently protrude from applicator 20, while in some embodiments, needles 17 may be configured to retract into applicator 20. For example, needles 17 may be retracted into applicator 20 during insertion of the applicator into a body cavity and then projected through openings 14 once in place.

Needles 17 may be formed of any suitable material, including, e.g., glass, plastic (with or without fillers, e.g., liquid silicone rubber, polyetheretherketone, polyphenylsulfone, polycarbonate, and/or polyoxymethylene), ceramic, metal (e.g., types of stainless steel, titanium, nitinol), or any suitable combination of materials. For example, needles 17 may be comprised of two or more different materials. In some embodiments, the tip may be formed of a material that is harder than the base portion of the needle. Needles 17 may also include a marker capable being imaged via an imaging device to assist a clinician with needle insertion or to check insertion depth or location before, during, or after a treatment procedure. In other embodiments, the entire needle may be formed of the same material. Additionally, needles 17 may include any suitable coating, or any suitable combination of coatings. For example, a coating may be lubricious, drug eluting, anticoagulant, antiseptic, or anesthetic. Needles 17 may further be filled with an obturator during insertion of the needle into the patient to increase the stiffness of the needle temporarily. For example, the needle may be filled with a material, such as tungsten, stainless steel, spring steels, or any suitable material or alloy thereof, to block an opening in the needle as it is introduced to the body. Needle 17 may be monolithically formed, or alternatively, needle 17 may be formed of separate parts made of the same or different materials, for example, plastic-coated glass needles. Needles 17 may be removable from or permanently coupled to applicator body 12 and/or catheters 13.

Creating a customized applicator 20 may allow a clinician to deliver a more accurate dosage of treatment during a treatment session and to provide a more customized treatment plan tailored to the needs of the individual patient. Custom applicator 20 may give the clinician more control over the dose distribution and may offer the patient a more effective and personalized treatment regimen. Applicator production process 50 may allow manufacturers or clinicians to quickly and efficiently generate customized applicators for practical use.

The many features and advantages of the present disclosure are apparent from the detailed specification, and thus, it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A method of forming an applicator body of an applicator for insertion into an anatomical cavity of a patient for delivering a treatment to the patient, the method comprising:
   receiving a first three-dimensional image of the anatomical cavity, the first three-dimensional image having been generated while the anatomical cavity contained an expandable container adjacent a tissue region of the patient, wherein the expandable container, when contained in the anatomical cavity, was filled with a fluid such that the container was expanded to substantially conform to the shape of at least a portion of the tissue region forming at least a portion of the anatomical cavity;
   isolating, from the first three-dimensional image, a first sub-image corresponding to an image of the filled expanded container; and
   using the first sub-image as a design template for forming the applicator body for use with the patient.

2. The method of claim 1, further comprising:
   sending the first sub-image to a three-dimensional printer to form the applicator body; and
   forming the applicator body with the three-dimensional printer, using the first sub-mage as the design template for the three-dimensional printer.

3. The method of claim 1, wherein the first three-dimensional image is a magnetic resonance image.

4. The method of claim 1, wherein the anatomical cavity is a vaginal cavity.

5. The method of claim 1, wherein the applicator is configured to deliver a dose of treatment to the tissue region.

6. The method of claim 5, wherein the applicator is a brachytherapy applicator and the treatment is radiation.

7. The method of claim 1, wherein the fluid is saline.

8. The method of claim 1, further comprising:
   receiving a second three-dimensional image of the expanded container, isolating from the second three-dimensional image a second sub-image, and using the second sub-image and the first sub-image as the design template to form the applicator body.

9. The method of claim 8, wherein the first three-dimensional image is all image of the anatomical cavity taken with the container expanded to a first pressure, and the second three-dimensional image is an image of the anatomical cavity taken with the container expanded to a second pressure different from the first pressure.

10. The method of claim 1, wherein using the first sub-image as a template for forming the applicator body further includes:
    processing data from the first sub-image to determine the location of at least one feature of the applicator body that is used for delivery of treatment to the patient.

11. The method of claim 10, wherein the at least one feature includes a channel for delivering the treatment via the applicator body to the patient.

12. The method of claim 11, wherein the channel is configured to guide at least one of a catheter and a needle to a portion of the region of tissue in the anatomical cavity.

13. The method of claim 10, wherein the at least one feature includes an opening in the applicator body that is configured to deliver the treatment.

14. The method of claim 10, wherein the processing includes the use of at least one algorithm for determining the location of the at least one feature of the applicator body.

15. The method of claim 10, wherein the at least one feature is formed by the three-dimensional printer when forming the applicator body.

16. The method of claim 10, wherein the at least one feature is formed after the three-dimensional printer has formed the applicator body.

17. The method of claim 12, further comprising:
    inserting at least one of the catheter and the needle in at least one channel after the applicator body is formed.

18. A method of forming an applicator body to be used for providing radiation treatment to a patient, comprising:
    placing an expandable container into a body cavity of a patient;
    filling the expandable container with fluid such that the container expands to fill the body cavity, and an external surface of the container substantially conforms to the shape of the body cavity;
    obtaining a first image of the expanded container placed in the patient;
    using a shape of the expanded container in the first image to determine the shape of the body cavity; and
    configuring an overall shape of the applicator body based on the determined shape of the body cavity.

19. The method of claim 18, further comprising:
    determining a location of at least one treatment channel in the applicator body for delivering the radiation treatment to the patient, wherein the location of the treatment channel is determined based on the determined shape of the body cavity and based on a determined location in the first image of an anatomical portion of the patient requiring treatment.

20. The method of claim 19, further comprising:
    determining a number of treatment channels to be included in the applicator body based on the determined shape of the body cavity from the first image.

* * * * *